United States Patent
Kim et al.

(10) Patent No.: US 10,874,484 B2
(45) Date of Patent: Dec. 29, 2020

(54) IMAGE PROCESSING METHOD FOR ORTHODONTIC PLAN, DEVICE AND RECORDING MEDIUM THEREFOR

(71) Applicant: OSSTEMIMPLANT CO., LTD., Seoul (KR)

(72) Inventors: Seong Gon Kim, Seoul (KR); Jeong Ho Choi, Seoul (KR); Byoung Ho Kim, Seoul (KR)

(73) Assignee: OSSTEMIMPLANT CO., LTD., Seoul (KR)

(*) Notice: Subject to any disclaimer, the term of this patent is extended or adjusted under 35 U.S.C. 154(b) by 107 days.

(21) Appl. No.: 15/754,042

(22) PCT Filed: Aug. 24, 2016

(86) PCT No.: PCT/KR2016/009391
§ 371 (c)(1),
(2) Date: Feb. 21, 2018

(87) PCT Pub. No.: WO2017/039220
PCT Pub. Date: Mar. 9, 2017

(65) Prior Publication Data
US 2018/0235729 A1 Aug. 23, 2018

(30) Foreign Application Priority Data
Aug. 31, 2015 (KR) .................. 10-2015-0122442

(51) Int. Cl.
*G06T 7/00* (2017.01)
*A61C 7/00* (2006.01)
(Continued)

(52) U.S. Cl.
CPC ............... *A61C 7/002* (2013.01); *A61B 1/24* (2013.01); *G06T 5/006* (2013.01); *G06T 7/0012* (2013.01);
(Continued)

(58) Field of Classification Search
CPC .............. A61C 7/002; G06T 7/0012; G06T 2207/30201; G06T 2207/30041;
(Continued)

(56) References Cited

U.S. PATENT DOCUMENTS

| 8,879,804 B1 | 11/2014 | Konoplev et al. |
| 2009/0060290 A1* | 3/2009 | Sabe ............ G06K 9/00248 382/118 |

(Continued)

FOREIGN PATENT DOCUMENTS

| JP | 2013-98840 | 5/2013 |
| KR | 2000-0054862 | 9/2000 |

(Continued)

OTHER PUBLICATIONS

English translation of the Written Opinion of International Application No. PCT/KR2016/009391, dated Mar. 6, 2018.

(Continued)

*Primary Examiner* — John W Lee
(74) *Attorney, Agent, or Firm* — Kile Park Reed & Houtteman PLLC (57) ABSTRACT

The present invention relates to an image processing method for orthodontic planning, a device and a recording medium therefor. The image processing method according to the present invention corrects the patient image to be horizontal and provides grids for analyzing the facial symmetry of the patient. According to the method, it decreases time for processing the patient image and inconvenience of the user and it helps to make the orthodontic plan considering the symmetry.

12 Claims, 6 Drawing Sheets

(51) Int. Cl.
*G06T 5/00* (2006.01)
*A61B 1/24* (2006.01)

(52) U.S. Cl.
CPC ............... *G06T 2207/10116* (2013.01); *G06T 2207/20021* (2013.01); *G06T 2207/30036* (2013.01); *G06T 2207/30041* (2013.01); *G06T 2207/30201* (2013.01)

(58) Field of Classification Search
CPC . G06T 2207/30036; G06T 2207/10116; G06T 5/006; G06T 2207/20021; A61B 1/24
See application file for complete search history.

(56) References Cited

U.S. PATENT DOCUMENTS

2010/0014755 A1* 1/2010 Wilson ............... G06K 9/00604
382/173

2014/0160263 A1* 6/2014 Reisman ................. G16H 50/70
348/78
2014/0292749 A1* 10/2014 Vaganov ............. G06F 3/04815
345/419

FOREIGN PATENT DOCUMENTS

| KR | 10-0857463 | 9/2008 |
| KR | 10-0982171 | 9/2010 |
| KR | 10-1501410 | 3/2015 |

OTHER PUBLICATIONS

International Search Report for International Application No. PCT/KR2016/009391, dated Dec. 8, 2016.

* cited by examiner

Before Correction         After Correction

IMAGE PROCESSING METHOD FOR ORTHODONTIC PLAN, DEVICE AND RECORDING MEDIUM THEREFOR

TECHNICAL FIELD

The present invention relates to an image processing method for orthodontic planning, a device and a recording medium therefor. More specifically, the present invention relates to the method which processes a patient image so that a user can easily analyze the patient image when planning the dental orthodontic treatment with software, the device, and the recording medium therefor.

BACKGROUND ART

The orthodontic treatment is for correcting uneven teeth or malocclusion.

The orthodontic treatment plan is made based on an X-ray film image for checking teeth or bone structure and also a facial image taken of the patient's face. When taking the facial image, there could be abnormal cases that the facial image is crooked or tilted off from the horizontal line due to misalignment of the patient and camera. In those cases, according to the prior arts, user rotates or moves the image depending on his own decision to get the image adjusted horizontally. However, not only is this method inaccurate, it may lead to wrong orthodontic treatment plan in the end.

For the orthodontic treatment, it is important not only to correct the teeth arrangement but also to get it harmonized with the overall impression of the face. In order to maximize patient's satisfaction after the treatment, it needs a process in the orthodontic treatment planning to analyze the arrangement of the teeth, the symmetry of the overall face including jaw, and the degree of the asymmetry. So, the user synthetically analyzes specific positions of eyes, ears, a nose, a mouth, and teeth etc. and the symmetric relationship between them based on the patient image, and then makes the orthodontic treatment plan with the analysis result.

However, when the user makes the orthodontic treatment plan based on the patient image with the orthodontic software, most of existing programs do not provide any tool for analyzing symmetry of overall face.

If any, it displays unchangeable reference guidelines of the symmetry and requires the user to move the patient image here and there to align with the reference guidelines, which causes great inconvenience of the users and delay of the orthodontic planning in the end. Also, because the reference guidelines are predefined according to the kind of the patient images like a frontal image, and a side image, the user has to use only the predefined kind of image according to the reference guidelines.

Therefore, a patient image processing method is needed that the user can modify accurately the image to correct errors due to misalignment of the patient, and make the orthodontic plan easily considering the symmetry in order to increase patient's satisfaction.

DETAILED DESCRIPTION OF THE INVENTION

Technical Problem

The present invention is to overcome aforementioned problems of the prior arts that have incorrectness when modifying the patient image or planning orthodontic treatment considering facial symmetry and cause a lot of inconvenience to the user.

Therefore, the object of the present invention is to provide a method for processing the patient image in order that the user can analyze easily the patient image in orthodontic treatment planning, and a device, and a computer-readable recording medium therefor.

Technical Solution

In order to achieve the above object, an image processing method for orthodontic planning, includes steps of correcting a patient image by rotating the patient image so that two eyes on the patient image are arranged horizontally; generating a grid on the corrected patient image to divide the corrected patient image by grid cells; and displaying the corrected patient image and the grid on a display unit.

The step of correcting the patient image may include rotating the patient image by an angle between a straight line passing two points in both pupils on the patient image and a horizontal line passing a midpoint between the two points.

The step of generating the grid may include steps of dividing equally a length between two points in both pupils on the patient image by a predetermined number; and generating a first grid, each grid cell of which has a unit size resulted by equally dividing the length.

In addition, the step of generating the grid may further include generating a second grid by grouping a predetermined number of the grid cells in the first grid as a grid cell of the second grid so as to start from a vertical line passing a midpoint between the two points in both pupils.

The step of generating the grid may further include generating a third grid by dividing each grid cell of the first grid into a predetermined number of the grid cells.

Herein, the third grid can be generated inside only a cursor-placed grid cell of the first grid where the cursor is put on the patient image enlarged more than a predetermined magnification.

Furthermore, in order to achieve the above object, an image processing device for orthodontic planning includes an image correction unit for correcting a patient image by rotating the patient image so that two eyes on the patient image are arranged horizontally; a grid generation unit for generating a grid on the corrected patient image to divide the corrected patient image by grid cells; and a display unit displaying the corrected patient image and the grid.

The image correction unit takes two points in both pupils on the patient image from a user through a user input unit or detects two points in both pupils by analyzing the patient image, and rotates the patient image based on the two points which are taken or detected.

The grid generation unit generates a new grid by grouping a predetermined number of grid cells in the generated grid as a grid cell of the new grid, or dividing each of grid cells of the generated grid into a predetermined number of the grid cells.

The grid generation unit generates the grid by distributing residual pixels equally in the grid cells positioned symmetrically with respect to vertical reference line passing a midpoint between two points in both pupils on the patient image, the residual pixels being the pixels which don't belong to any grid cell with dividing the patient image in the grid cells of equal size.

The grid generation unit provides options for selecting a grid level defined according to a size of the grid cell.

In order to achieve the above object, a computer-readable recording medium have a program to execute the above image processing method for orthodontic planning.

Effects of the Invention

As stated above, according to the present invention, it decreases time for processing the patient image and inconvenience of the user and it helps to make the orthodontic plan based on the symmetry by correcting of the patient image and generating grids.

In addition, according to the present invention, various multiple grids are provided so that the user can analyze with an appropriate grid according to the certain patient and condition, thereby contributing to patient-specific orthodontic treatment planning.

BEST MODE FOR CARRYING OUT THE INVENTION

Hereinafter, with reference to the accompanying drawings, preferred embodiments of the present invention will be described in detail. However, the explanation on the known functions and configurations that may obscure the subject matter of the present invention from the detailed description of the following description and from the accompanying drawings will be omitted. In addition, it needs to be noted that the same components throughout the drawings are referred to by the same reference numerals as possible.

The terms used in this specification and claims is not to be construed as limited to dictionary meanings, but can be defined and interpreted based on the meanings and concepts corresponding to technical aspects of the present invention in the principle that inventors define the terms appropriate to the concept of a term to describe his own invention in the best way. Therefore, the present embodiment and the configuration shown in the drawings and described in the specification is merely nothing but a preferable embodiment of the present invention, as not intended to represent all the technical concept of the present invention, so that it should be understood that many equivalents and varied modified embodiments of the present invention can exist at the time of the present application point.

A patient image, written on this specification, is an image taken the whole or part of the patient's face including eyes for orthodontic treatment. The patient image includes a two-dimensional image, a three-dimensional image, and a multi-dimensional image more than three dimension.

Hereinafter, it is explained with two-dimensional image as an example of the patient image.

Figure 1:
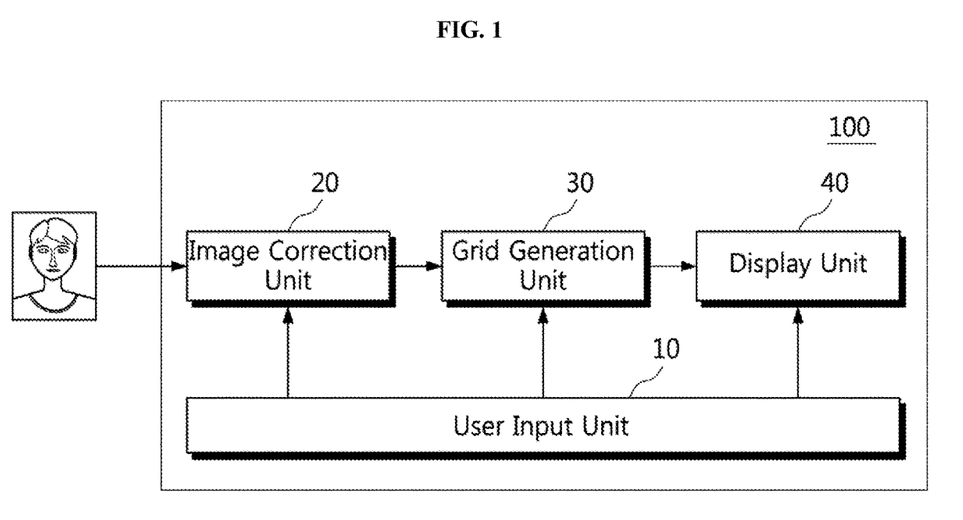
FIG. 1 is a block diagram of an image processing device for orthodontic planning according to an embodiment of the present invention.

FIG. 1 is a block diagram of an image processing device for orthodontic planning according to an embodiment of the present invention.

Referring to FIG. 1, the image processing device for orthodontic planning 100 comprises a user input unit 10, an image correction unit 20, a grid generation unit 30, and a display unit 40.

The user input unit 10 is means for accepting various necessary inputs from the user in process of dental orthodontic planning. The user input unit 10 can be implemented with various input devices including a mouse, a keyboard, a joystick, and a digitizing pad, etc. The patient image, selected through the user input unit 10 by the user, is loaded. The user enters various processing commands regarding the loaded image through the user input unit 10.

The image correction unit 20 rotates the patient image a certain angle so that two eyes on the patient image are arranged horizontally. As a result, the patient image, which has been taken to be tilted off from the horizontal line due to misalignment of the patient and camera, can be corrected uprightly. The image correction unit 20 can use two points in both pupils on the patient image as reference of the rotation. The two points can be selected among the points positioned correspondingly in both pupils.

The grid generation unit 30 generates a grid in shape of a checkerboard, which divides the patient image corrected by the image correction unit 20. The grid generation unit 30 generates the grid by dividing the corrected patient image with grid cells of a certain size. For reference, the grid cell, a unit of the grid, forms rows and columns of the grid and has a shape of square.

The grid generation unit 30 can generate multi-level grids so that the user can analyze the symmetry of the patient's face correctly. The grid level is defined to represent a size of the grid cell which is a unit of the grid. Explaining an example of the grid level, in case the grid generation unit 30 generates the grids of from level 1 to level 3, and the level 1 is a basic size of the grid cell, the higher the grid level goes up the bigger or smaller the size of the gird cell becomes.

Figure 2:
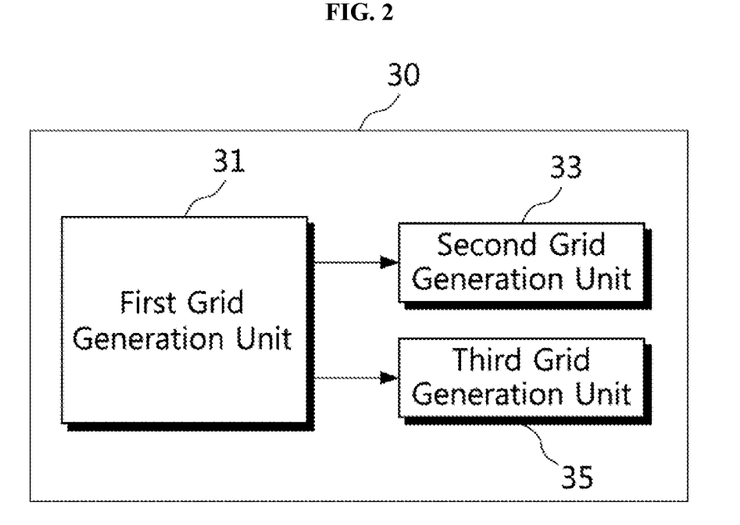
FIG. 2 is a block diagram showing an exemplary of detail components of a grid generation unit illustrated in FIG. 1.

In this regard, referring to FIG. 2, which is a block diagram showing an exemplary of detail components of the grid generation unit 30, the grid generation unit 30 can be subdivided into a first grid generation unit 31, a second grid generation unit 33, and a third grid generation unit 35.

The first grid generation unit 31, the second grid generation unit 33, and the third grid generation unit 35 generate a first grid, a second grid, and a third grid each. For reference, the terms of the first grid, the second grid, and the third grid is for distinguishing each of the grids having different size of grid cells, and the order of those names is irrelevant to the size of the grid cells.

The first grid generation unit 31 generates the first grid, each grid cell of which has a unit size resulted by equally dividing a length between two points in both pupils on the patient image by a predetermined number. For example, in case the unit size equally divided is 5 mm, the first grid is consisted of grid cells of 5 mm in width, and 5 mm in length.

The second grid generation unit 33 generates the second grid by grouping a predetermined number of the grid cells in the first grid as a grid cell of the second grid.

The third grid generation unit 35 generates the third grid by dividing each grid cell of the first grid into a predetermined number of the grid cells.

The grid generation unit 30 can generate the grid according to a certain level determined in advance. Or the grid generation unit 30 can provide options for selecting the level of the grid to the user to accept the desired level of the grid through the user input unit 10, and can generate the grids having grid cells of various sizes by merging, dividing, or combination of merging and dividing the grid cells of the generated grid.

The display unit 40 displays various options or screens for providing necessary information in dental orthodontic planning including the patient image corrected to be horizontal by the image correction unit 20 and the grid generated by the grid generation unit 30.

Figure 3:
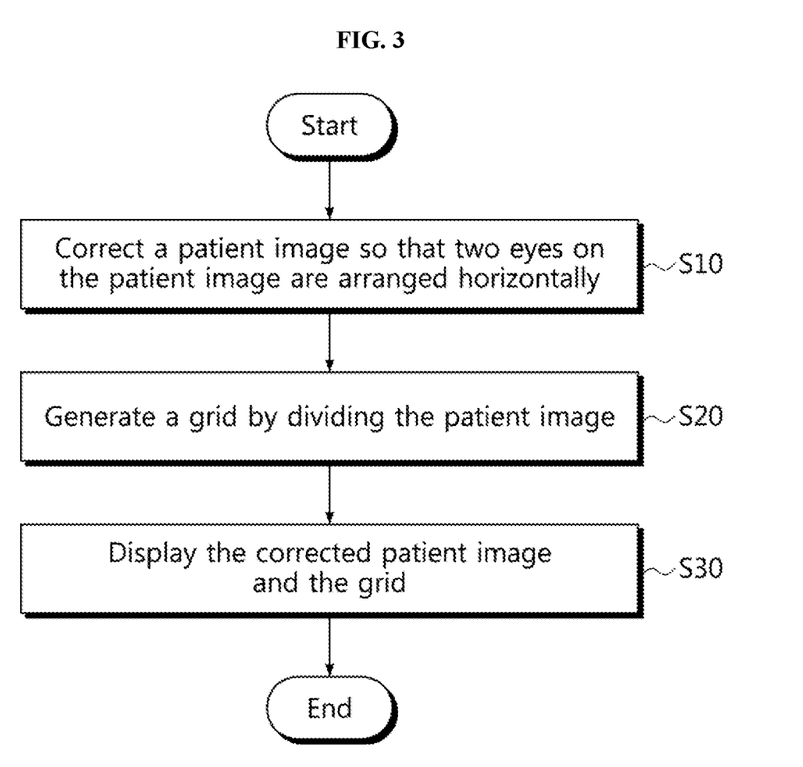
FIG. 3 is a flowchart that depicts an image processing method for orthodontic planning according to an embodiment of the present invention.
Figure 4:
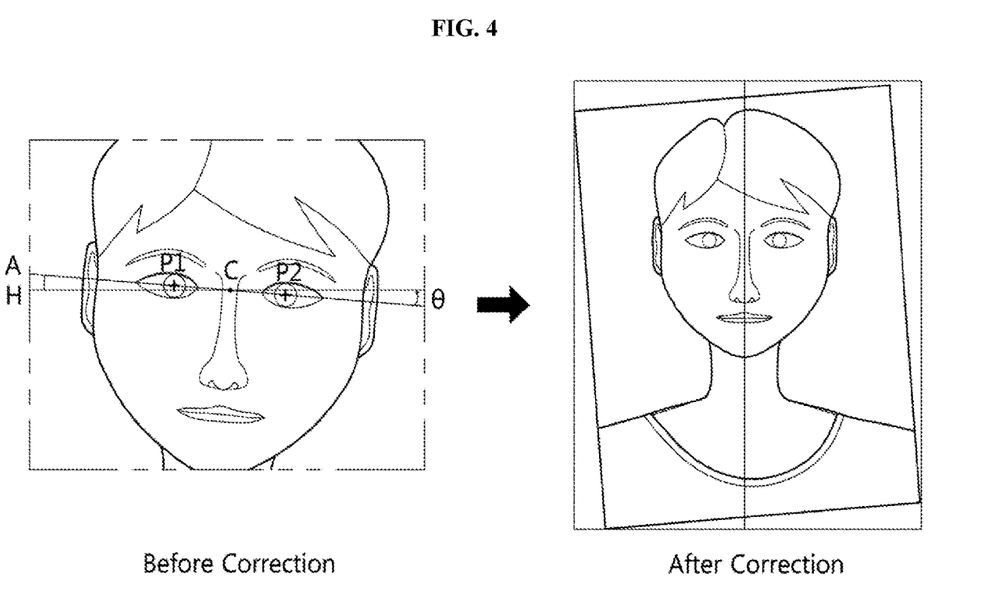
FIG. 4 is a drawing for explaining an exemplary of a method for correcting the patient image horizontally.
Figure 5:
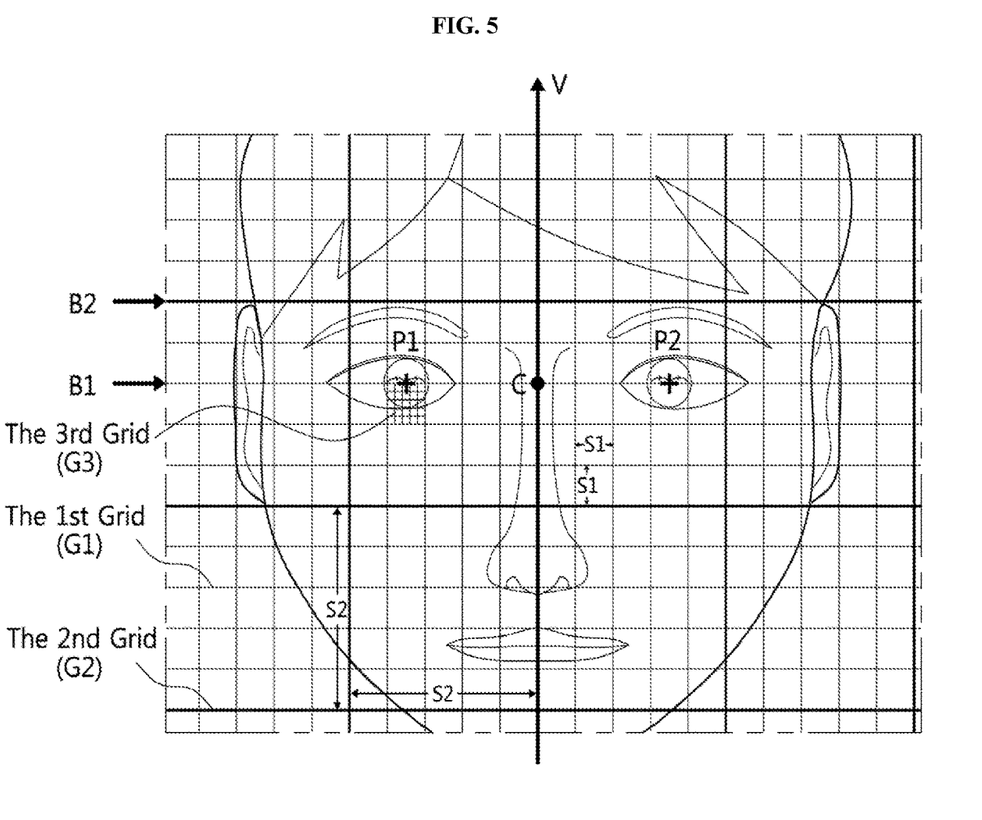
FIG. 5 is a drawing for explaining an exemplary of a method for generating grids on the patient image.
Figure 6:
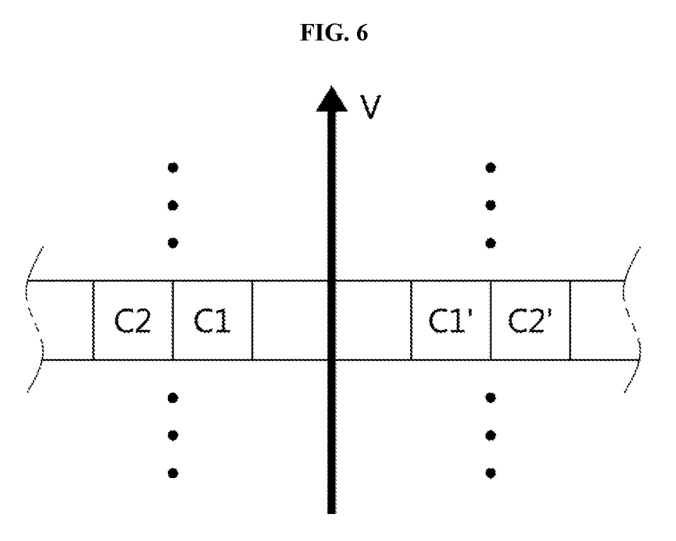
FIG. 6 is a drawing for explaining an exemplary of a method for processing residual pixels of the image in process of generation the grids.

FIG. 3 is a flowchart that depicts an image processing method for orthodontic planning according to an embodiment of the present invention, and FIG. 4 to FIG. 6 are for explaining examples according to respective processes in image processing. Hereinafter, with referring to FIG. 3 and FIG. 4 to FIG. 6, the systematic operations of components of the image processing device 100 shown in FIG. 1 will be described.

When the patient image for orthodontic planning is obtained through the imaging apparatus, the image correction unit 20 corrects the patient image by rotating the patient image so that two eyes on the patient image are arranged horizontally in step S10.

FIG. 4 is a drawing for explaining an exemplary of a method for correcting the patient image horizontally. Referring to the patient image before correction in FIG. 4, the patient image has been taken to be tilted off from the horizontal line due to misalignment of the patient.

The image correction unit 20 corrects the patient image by rotating the patient image based on two points P1, P2 positioned each in both pupils. When rotating the patient image, the angle of the rotation Θ can be calculated as an angle between a straight line A passing the two points P1, P2 and a horizontal line H passing a midpoint C between the two points P1, P2.

To select corresponding points in each pupil as the two points P1, P2, which are reference points of rotation, common regional parts of the both pupils are referenced. As an example of the common regional part for selecting the two points, an image projected inside both pupils by light emitted from a camera when taking a picture can be applied. In addition, the two points P1, P2 can be entered directly from the user through the user input unit 10 or can be automatically detected inside both pupils by analyzing the patient image. For the automatic detection of the two points P1, P2, various image detection algorithms can be applied.

Referring to the patient image after correction in FIG. 4, it can be confirmed that the patient image has been corrected so that two eyes on the patient image are arranged horizontally.

As mentioned above, after correcting the patient image horizontally, the grid generation unit 30 generates the grid for helping to analyze the symmetry of the patient image in step S20. The grid is generated by dividing the corrected patient image by grid cells.

FIG. 5 is a drawing for explaining an exemplary of a method for generating grids on the patient image. Referring to FIG. 5, an example of generating three kinds of grids will be described.

The first grid generation unit 31 equally divides a length between P1 and P2 by a predetermined number, and generates the first grid G1, each grid cell of which has a unit size S1 resulted by equally dividing the length between the two points P1, P2.

As an example of generation of the first grid G1, as shown in FIG. 5, the first grid generation unit 31 can arrange two points P1, P2 so that P1, P2 are positioned on a borderline B1 of the first grid G1 and also P1, P2 are positioned each on the center of one side of the grid cell. And the first grid generation unit 31 can generate the first grid G1 by dividing the patient image by the unit size S1 with reference to P1 and P2. The position of P1 and P2 on the first grid G1, shown in FIG. 5, is only an example. Therefore, the position of P1 and P2 can be decided differently from the position mentioned above. For example, P1 and P2 can be positioned on the center of mass of the grid cell of which shape is a square.

In reference, in FIG. 5, although the example is shown that the length between P1 and P2 is equally divided by seven, the number of division can be varied according to the size of the patient image or the selection of the user. Furthermore, the criterion for deciding the number of division can be made in advance, and the number of division can be decided flexibly according to the criterion, thereby satisfying individual characteristic of the patient. For example, for the patient who has long length between P1 and P2, the relatively bigger number of division can be applied. On the other hand, for the patient who has short length, the relatively smaller number of division can be applied.

The second grid generation unit 33 generates the second grid G2 by grouping a predetermined number of grid cells of the first grid G1 as one grid cell of the second grid G2. That is, the second grid generation unit 33 determines the size of new grid cell which equals to the total size of a predetermined number of the grid cells of the first grid G1 and merges the grid cells of the first grid G1 by the predetermined number of the grid cells, which starts at a vertical line V passing a midpoint C between P1 and P2, to generate a second grid G2 composed of the new grid cells.

For example, FIG. 5 shows that a horizontal line B2 is used as the other starting line of merging for the second grid G2 and the border line of the grid cell above P1 and P2 is selected as B2 among multiple horizontal border lines of the first grid G1.

In addition, in FIG. 5, although the example is shown that five grid cells of the first grid G1 in length and width are grouped to generate the second grid G2, the number of grid cells to be grouped can be decided differently. For example, the number of grid cells to be grouped can be varied based on the size of the patient image or the selection of the user, in the same manner as the first grid G1.

And then, the third grid generation unit 35 generates the third grid G3 by dividing each grid cell of the first grid G1 into a predetermined number of grid cells. As a result, the third grid G3 consists of grid cells generated from the division of the first grid G1. In FIG. 5, although the example is shown that the third grid G3 is generated by dividing each grid cell of the first grid G1 into five grid cells each in length and width, the division number of grid cell can be varied.

As illustrated in FIG. 5, the third grid generation unit 35 can generate the third grid G3 inside only a cursor-placed grid cell of the first grid G1 where the cursor is put. In addition to the position of the cursor as a condition of generation of the third grid G3, the third grid generation unit 35 can generate the third grid G3 only when the patient image is enlarged more than a predetermined magnification. For example, the third grid generation unit 35 can generate the third grid G3 inside only the cursor-placed grid cell of the first grid G1 on the patient image enlarged more than double size.

As mentioned above, in FIG. 5, although it is assumed that the grid generation unit 30 generates three grids G1, G2, G3, the grid generation unit 30 can generate multi-level grids of the various size of grid cell by grouping, dividing, or combination of grouping and dividing grid cells of the generated grid according to the user input through the user input unit 10 or settings of the image processing device 100.

Because the patient image consists of pixels, there could be a case that the size and number of the grid cells might not make the grid cells include all the pixels of the patient image. In this case, some residual pixels which do not belong to any grid cell would be generated. In order that no residual pixel is generated, the grid generation unit 30 adjusts the size of some grid cells so as to make the size of the grid cells unequal and all the pixels of the patient image belong to some grid cells. The grid generation unit 30 can generate the grid by distributing the residual pixels to a random grid cell. However, doing this, it is likely to stand out the difference in size from other grid cells which no residual pixel is given when the patient image is enlarged or reduced.

Therefore, in order to minimize the difference of size and keep a balance of size between grid cells, the grid generation unit 30 can select grid cells which are pair or symmetric with respect to vertical line V as the grid cells to be adjusted.

FIG. 6 is a drawing for explaining an exemplary of a method for processing residual pixels of the image in process of generation the grids by division.

For example, assuming that the grid generation unit 30 equally divides a certain length by seven and generates the grid, each grid cell of which has a unit size resulted by equally dividing the length, residual pixels can be produced from one to six. The example is shown that four residual pixels exist in FIG. 6.

Referring to FIG. 6, the grid generation unit 30 can distribute one residual pixel each to grid cells C1 and C1' which are symmetric with respect to the vertical line V. In the same manner, the grid generation unit 30 can distribute one residual pixel each to grid cells C2 and C2' which are symmetric with respect to the vertical line V.

FIG. 6 shows only an example for distributing residual pixels, so, if residual pixels can be distributed equally with respect to the vertical line V, various distribution algorithms can be applied. For example, the residual pixels can be distributed first to the far side from the vertical line V. That is, the residual pixels can be distributed first to grid cells far from the vertical line V, and then distributed to grid cells near from the vertical line V.

After correcting the image and generating the grid through the steps mentioned above, the corrected patient image and the generated grid are provided to the user by display unit 40 in step 30. The user can analyze the symmetry for orthodontic planning based on the screen on the display unit 40. The display unit 40 can display only desired grid selectively among the generated grids according to the user input through the user input unit 10. In addition, the display unit 40 can provide options for selecting color, style of lines, and thickness of lines, etc. for each grid, and can display each grid to be identified by its color, style of lines, and thickness of lines, etc. according to the selection of the user through the user input unit 10.

The steps mentioned above can be appropriately added or modified as needed. For example, a step that the grid generation unit 30 provides the user with options for selecting level of grid defined according to size of the grid cell can be added. And the grid generation unit 30 can be implemented to generate only the grid of the selected level.

On the other hand, the image processing method for orthodontic planning according to an embodiment of the present invention can be written in a program to run on the computer and can be implemented to a variety of recording medium such as magnetic storage medium, optical recording medium, or digital storage medium.

As can be seen from the above description, according to the embodiment of the present invention, the patient image can be automatically corrected to be horizontal and the tool for analyzing facial symmetry without cumbersome operations of the user is provided. Therefore, as compared to the conventional program for orthodontic planning, it is expected that the convenience of the user will be increased, and also the patient's satisfaction for the treatment will become higher.

Implementations of the various techniques described herein area digital electronic circuitry, or computer hardware, firmware, software, or may be implemented in a combination of them. Implementations can be implemented by a data processing device, for example, a programmable processor, a computer, or for processing by the operation of a plurality of computers, or to control the operation, the computer program product, i.e. the information carrier, for example, machine-readable apparatus (computer readable medium) or a radio signal. The computer program as stated above can be recorded in a programming language of any type, including a substituted or interpret compiled language, as a stand-alone program or as a module, component, subroutine, or in the computing environment, it may be deployed in any form, including as appropriate, including the use of other units. Computer program can be distributed across one or more computer or a number of sites to be processed on multiple computers at one site, and can be connected by a communication network.

Processors suitable for the processing of the computer program comprise as an example, includes both general and special purpose microprocessors, and more than one processors of any kind of digital computer. Generally, a processor may receive commands or data from read-only memory or random-access memory or both. The computer can include more than one memory device saving at least one processor and commands and data which executes commands. For example, it includes magnetism, magnetic-optical disks, or optical disks, or transmitting this data or combining both, or it can receive or transmit data or combine both. Information carriers appropriate for specifying computer program commands or data as an example, semiconductor memory device, for example, includes hard disks, floppy disks, and magnetic tape, such as magnetic media, CD-ROM (Compact Disk Read Only Memory), DVD (Digital Video disk) and the like optical recording media, floptical disk, such as magneto-optical media, ROM (Read Only Memory), RAM (Random Access memory), comprises a flash memory, EPROM (Erasable Programmable ROM), EEPROM (Electrically Erasable Programmable ROM) etc. Processor and memory can be added or included by special purpose logic circuitry.

The present description herein includes details a number of specific implementations, but it cannot be understood as limited for any invention or scope for patent claims, rather to be understand as explanation about featuring specific implementation of specific invention. The specific features of the present description in context of each implementation herein can be implemented in combination in a single embodiment. Conversely, it also can be implemented in a plurality of embodiments with different features, any suitable sub-combination or separately described in the context of a single embodiment. Furthermore, the features can be combined as specific combinations or described as claimed in early, but one or more features from claimed combinations can be excluded from the combination in some cases, the claimed combination can be changed as sub-combination or its modifications.

Likewise, although it describes operations as particular order, it cannot be understood that performing those operations as the specific or sequential order described to achieve desired results or being performed for all described operations. In certain case, multi-tasking and parallel processing can be advantageous. In addition, separation of various system components in the embodiments described above should not be understood to require in any embodiment such a separation, the described program components and systems are generally integrated together in a single software product or be packaged into multiple software products number that should be understood.

On the other hand, the embodiments of the invention disclosed in the specification and drawings are not presented merely a specific example for clarity and are not intended to limit the scope of the invention. It addition to the embodiments disclosed herein another modification based on the technical ideas of the invention are possible embodiments, it will be apparent to those of ordinary skill in the art.

What is claimed is:

1. An image processing method for orthodontic planning, comprising:
    correcting a patient image by rotating the patient image so that two eyes on the patient image are arranged horizontally;
    dividing equally a length between two points located respectively in both pupils on the patient image by a predetermined number, wherein the predetermined number is determined to be proportional to the length between the two points;
    generating a first grid, each grid cell of which has a unit size resulted by equally dividing the length;
    generating a second grid by grouping a predetermined number of the grid cells in the first grid as a grid cell of the second grid so as to start from a vertical line passing a midpoint between the two points in both pupils;
    generating a third grid by dividing each grid cell of the first grid into a predetermined number of the grid cells;
    displaying the corrected patient image, the first grid, the second grid, and the third grid on a display,
    wherein the first grid is generated so that each of the two points is positioned on the center of one borderline of the grid cell of the first grid.

2. The method according to claim 1, wherein correcting the patient image comprises,
    rotating the patient image by an angle between a straight line passing the two points in both pupils on the patient image and a horizontal line passing a midpoint between the two points.

3. The method according to claim 1,
    wherein the third grid is generated inside only a cursor-placed grid cell of the first grid where the cursor is put on the patient image enlarged more than a predetermined magnification.

4. An image processing device for orthodontic planning, comprising:
    an image corrector that corrects, by a processor, a patient image by rotating the patient image so that two eyes on the patient image are arranged horizontally;
    a grid generator that generates, by a processor, a first grid, a second grid, and a third grid on the corrected patient image; and
    a display that displays the corrected patient image, the first grid, the second grid, and the third grid,
    wherein
    the grid generator divides equally a length between two points located respectively in both pupils on the patient image by a predetermined number, wherein the predetermined number is determined to be proportional to the length between the two points,
    generates the first grid, each grid cell of which has a unit size resulted by equally dividing the length, wherein the first grid is generated so that each of the two points is positioned on the center of one borderline of the grid cell of the first grid,
    generates the second grid by grouping a predetermined number of the grid cells in the first grid as a grid cell of the second grid so as to start from a vertical line passing a midpoint between the two points in both pupils, and
    generates the third grid by dividing each grid cell of the first grid into a predetermined number of the grid cells.

5. The device according to claim 4, wherein the image corrector takes the two points in both pupils on the patient image from a user through a user input unit or detects the two points in both pupils by analyzing the patient image, and rotates the patient image based on the two points which are taken or detected.

6. The device according to claim 4, wherein the grid generator generates the grid by distributing residual pixels equally in the grid cells positioned symmetrically with respect to vertical reference line passing a midpoint between two points in both pupils on the patient image, the residual pixels being the pixels which don't belong to any grid cell with dividing the patient image in the grid cells of equal size.

7. The device according to claim 4, wherein the grid generator provides options for selecting a grid level defined according to a size of the grid cell.

8. A non-transitory computer-readable recording medium having a program to execute the image processing method for orthodontic planning according to claim 1.

9. A non-transitory computer-readable recording medium having a program to execute the image processing method for orthodontic planning according to claim 2.

10. A non-transitory computer-readable recording medium having a program to execute the image processing method for orthodontic planning according to claim 3.

11. The method according to claim 1, wherein the correcting the patient image comprises:
    taking the two points in both pupils on the patient image from a user through a user input unit or detecting the two points in both pupils by analyzing the patient image; and
    rotating the patient image based on the two points which are taken or detected.

12. The method according to claim 1, further comprises providing options for selecting a grid level defined according to a size of the grid cell.

* * * * *